(12) United States Patent
Kocak et al.

(10) Patent No.: US 8,680,319 B2
(45) Date of Patent: Mar. 25, 2014

(54) METHOD FOR PRODUCING ANTIFOLATE AGENTS HAVING GLUTAMIC ACID PART IN THEIR STRUCTURE

(75) Inventors: Ender Kocak, Istanbul (TR); Tuncer Aslan, Istanbul (TR)

(73) Assignee: Kocak Farma Ilac ve Kimya San. A.S, Istanbul (TR)

( * ) Notice: Subject to any disclaimer, the term of this patent is extended or adjusted under 35 U.S.C. 154(b) by 0 days.

(21) Appl. No.: 13/990,770

(22) PCT Filed: Dec. 3, 2010

(86) PCT No.: PCT/TR2010/000235
§ 371 (c)(1),
(2), (4) Date: May 30, 2013

(87) PCT Pub. No.: WO2012/074496
PCT Pub. Date: Jun. 7, 2012

(65) Prior Publication Data
US 2013/0253192 A1 Sep. 26, 2013

(51) Int. Cl.
*C07C 303/00* (2006.01)

(52) U.S. Cl.
USPC .......................................................... 560/12

(58) Field of Classification Search
USPC ............ 544/260; 562/571; 560/129, 155, 171
See application file for complete search history.

(56) References Cited

U.S. PATENT DOCUMENTS 3,035,041 A    5/1962   Schwyzer et al.

FOREIGN PATENT DOCUMENTS

WO        2006014706        2/2006

OTHER PUBLICATIONS

Endo et al. (Design and Synthesis of Photochemically Controllable Restriction Endonuclease BamHl by Manipulating the Salt-Bridge Network in the Dimer Interface, J. Org. Chem.vol. 69, 4292-4298, 2004).*
Loeffler L J et al: "Antineoplastic Agents. 2. Structure-Activity Studies on N-Protected Vinyl, 1,2-Dibromoethyl, and Cyanomethyl Esters of Several Amino Acids", Journal of Medicinal Chemistry, American Chemical Society, US, vol. 20, No. 12, Dec. 1, 1977. pp. 1584-1588.
International Search Report in International Application No. PCT/TR2010/000235 mailed on Aug. 9, 2011.
Written Opinion of the International Searching Authority in International Application No. PCT/TR2010/000235 mailed on Aug. 9, 2011.

* cited by examiner

*Primary Examiner* — Wu-Cheng Winston Shen
*Assistant Examiner* — Blaine G Doletski
(74) *Attorney, Agent, or Firm* — Abigail Smith; Oppedahl Patent Law Firm LLC

(57) ABSTRACT

A method for producing antifolate agents having glutamic acid part in their structure is developed by protecting carboxyl groups of glutamic acid or its N-substituted derivatives as cyanomethyl ester to give compounds of formula (II) which are hydrolyzed under very mild conditions to afford antifolate agents in high yield with high analytical and optical purity.

(II)

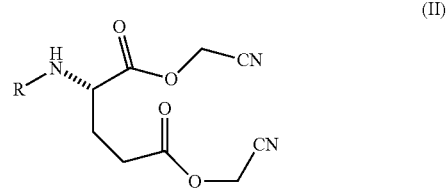

15 Claims, No Drawings

METHOD FOR PRODUCING ANTIFOLATE AGENTS HAVING GLUTAMIC ACID PART IN THEIR STRUCTURE

This invention relates to a new method for producing antifolate agents having glutamic acid part in their structure or salt thereof with the general formula

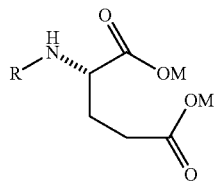
(I)

Wherein
M is a monovalent or divalent cation selected from group consisting of $Na^+$, $K^+$, $½Ca^{++}$ or $½Mg^{++}$; and
R is

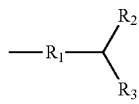
(II)

with
$R_1$ being a carbonyl group; and
$R_2$ and $R_3$ being the same or different and being selected from
straight-chain or branched, saturated or unsaturated $C_1$-$C_{20}$-heteroalkyl groups, which can optionally be substituted with amino groups;
aromatic or aliphatic $C_3$-$C_{18}$-hydrocarbon rings, which can optionally be substituted with one or more selected from the group consisting of alkyl, alkenyl, alkynyl, carboxy, hydroxy, amine, nitro, thiol, sulfoxy, sulfone groups, which can optionally be substituted and/or form further rings;
aromatic or aliphatic $C_3$-$C_{18}$-heterocycles, which can optionally be substituted with one or more selected from the group consisting of alkyl, alkenyl, alkynyl, carboxy, hydroxy, amine, nitro, thiol, sulfoxy, sulfone groups, which can optionally be substituted and/or form further rings;
whereby $R_2$ and $R_3$ together can form an aromatic or aliphatic $C_3$-$C_{18}$-heterocycle, which can optionally be substituted with one or more selected from the group consisting of alkyl, alkenyl, alkynyl, carboxy, hydroxy, amine, nitro, thiol, sulfoxy, sulfone groups, which can optionally be substituted and/or form further rings;
compressing reacting a compound of the following formula

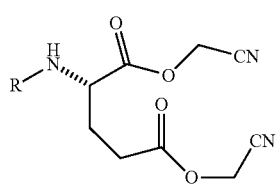
(II)

Wherein R is the same as in Formula (I), with an acid or base in an solvent; and the compounds of formula (II) are obtained from reacting glutamic acid, N-subsituted glutamic acids or their salts with chlorocetonitrile.

The compounds of Formula (I) form among others the backbone of a number of known antifolate agents, in which R is for example

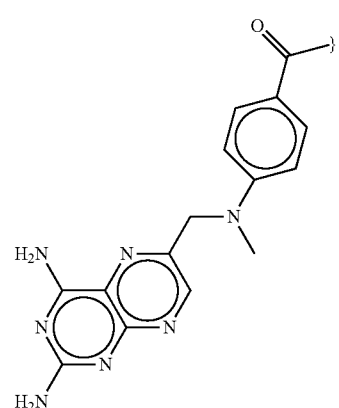
(III)

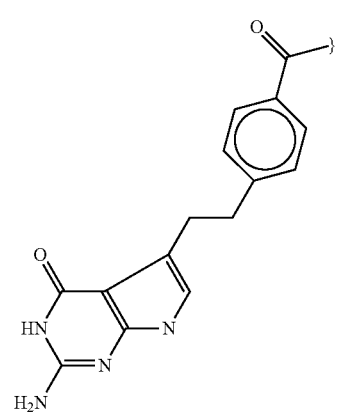
(IV)

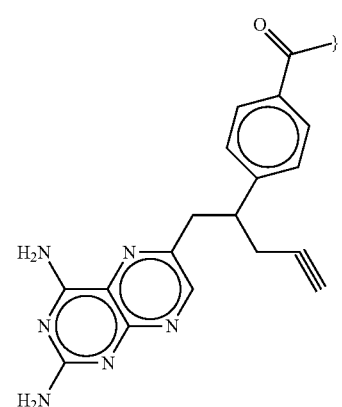
(V)

(VI)

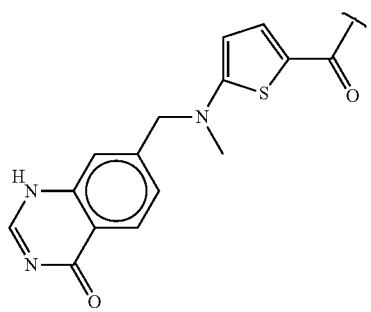

Folic acid inhibitors comprising such a heterocyclic aromatic backbone belong to a group of antimetabolites which are generally referred to as "antifolates". Antifolates which show such a heterocyclic aromatic backbone include Methotrexate (R is III), Pemetrexed (R is IV), Pralatrexate (R is V) and Raltitrexed (R is VI).

These agents work by inhibiting the action of key enzymes thymidylate synthase and dihydrofolate reductase and have found clinical utility as antitumor and antineoplastic agents. These agents inhibit both purine and pyrimidine synthesis by blocking enzyme functions and cause cell death. They have a greater toxic effect on rapidly dividing cell like cancer cells.

The new method for producing optically pure forms of the active pharmaceuticals can increase quality of the drug substances.

The compounds of Formula (II) include precursors to the above antifolates that are protected as a cyanomethyl ester and can be obtained deprotection of the cyanomethyl group on the glutamate moiety by using a basic or acidic agent.

U.S. Pat. No. 4,067,867 describes preparing well known potent folic acid antagonist methotrexate. In the last step of methotrexate synthesis diethyl N-[p[[(2-amino-3-cyano-5-pyrizinyl)methyl]methylamino]benzoyl]glutamate reacted with quanidine acetate in DMF to give Methotrexate diethyl ester. After purification it was found that the compound is completely racemic.

DE patent no 2824011 discloses preparation of p-(N-methyl-N-formyl)-aminobenzoyl-L-glutamic acid which is precursor in the synthesis of methotrexate. In the last step of synthesis formyl group is removed under basic conditions. They could not use strong alkali conditions and high temperature with long reaction time to remove formyl group because of the racemisation risk of the glutamic acid part of the molecule.

U.S. Pat. No. 4,136,101 describes for preparing dialkyl(p-methylaminobezoyl) glutamates from zinc N-(p-aminobezoyl)glutamates which is an intermediate in the synyhesis of Methotrexate. In the patent it states that due to the crystalline nature of zinc salt of the intermediate is cleaner than other metal salts. For example, the purity of the zinc N-(p-aminobezoyl)-L-glutamate is about 80-90% versus about 55-70% for the corresponding disodium salt. In this patent as lower alcohol like methanol, ethanol, 2-propanol and 1-butanol are used as solvent and treated with gaseous HCl under anhydrous conditions to get corresponding ester. Although this approach seems good there is still a racemization risk of the glutamate part during the hydrolysis of the ester moieties and use off corresive gaseous HCl together with expensive absolute alcohols makes this process unsuitable for a large scale synthesis.

There are also other patents and articles for preparing methotrexate directly from N-(p-aminobezoyl)-L-glutamic acid or its salts as an intermediate but in this case crude methotrexate obtained is not pure and need to be crystallized many times. These processes reduce the yield dramatically, (for example, the yield is below 6%, see J. Am. Chem. Soc. 1949, 71, 1753, the yield is 7%, see U.S. Pat. No. 3,989,703).

According to literatures given above it is difficult to produce Methotrexate in good yields with high analytical and optical purity. There is still a need to develop new synthetic routes for the preparation of antifolate agents.

Some of the compounds with different alkyl ester of the formula (II) are used as intermediates in the synthesis of the corresponding antifolates of formula (I) and need to be deprotected by hydrolysis at higher temperature under strong basic conditions to get active drug substances or their salt. But under these conditions there is a racemization risk at the alfa carbon of glutamic acid part and formation of the degradation products. When glutamic acid or their metal salts are used in the coupling reaction to get the antifolates, the yields are very low as mentioned above.

It is therefore an object of this invention to describe a new method for producing antifolate agents of formula (I) from compounds of formula (II) under very mild reaction conditions in good yield with high analytical and optical purity.

It was now surprisingly found that cyanomethyl group can be successfully used to protect carboxyl group of glutamic acid compounds of formula (II) which are intermediates in the synthesis of antifolates.

Cyanomethyl esters can be removed under very mild reaction conditions even serve as a living group in the coupling reaction of unnatural amino acids to dinucleotides during the preparation of misacylated transfer RNAs (Arslan et. al. J. Am. Chem. Soc. 1997, 119, 10877).

To get different alkyl ester of the formula (II) from the metal salt of glutamic acid, for example from zinc salt, it was necessary to carry out the reaction in absolute alcohol which is expensive and as acid source very corrosive gaseous HCl which is not convenient for large scale synthesis are used.

Another object of this invention is that cyanomethyl ester of the compounds of formula (II) or their intermediates having glutamic acid part can be easily prepared starting from metal salt of glutamic acid or from its N-substituted derivatives by reacting with chloroacetonitrile in a polar solvent.

Metal salts of glutamic acid that used as intermediates in the synthesis of compounds (I) cannot be obtained in pure form, for example, the purity of the zinc N-(p-aminobezoyl)-L-glutamate is about 80-90% versus about 55-70% for the corresponding disodium salt during the synthesis of methotrexate.

When cynomethyl ester of N-(p-aminobezoyl)-L-glutamate was prepared and isolated following the simple procedure in this invention, the purity of the intermediate is higher than 98% ($^1$H-NMR). The coupling reaction with pure intermediates gives pure compounds of formula (II) in the case of methotrexate with high yield It is yet an object of this invention is that cyanomethyl groups of formula (II) can be hydrolyzed under very mild basic or acidic conditions to give desired active substances or their salts in high yield with high analytical and optical purity.

Cyanomethyl ester act as protecting group of carboxyl functionalities of formula (II) but easily hydrolyzed at a more moderate pH value than previously used alkyl esters. They make also possible to obtain pure form of compounds (II) which result in pure antifolate agents of formula (I).

It is an embodiment of the invention, precursors of the antifolate agents having glutamic acid part is protected as dicynaomethyl esters reacting with chloroacetonitrile in a polar solvent and then coupled with other suitable intermediates to give protected antifolate agents as compounds of formula (II).

The compounds of the formula (II) are formed as intermediates in the synthesis of the corresponding antifolate agents of formula (I). In a further step, they need to be deprotected to form the desired active compounds of formula (I).

Preferably, $R_2$ and $R_3$ either together form a phenyl or thiophene ring, which are substituted with an alkyl group or alkyl group containing hetero atoms and alkyl groups are further substituted with bicyclic or heterocyclic aromatic ring systems containing structures like purines or pyrimidenes.

$R_1$ is preferably carbonyl.

Compounds of such a structure are known to show biological activity and therefore are of interest in the synthesis of drug substances for various pharmaceuticals In an embodiment of the invention, the compound of Formula (I) is a compound that shows antifolate activity and is used treating different type of cancers. Preferably, it is selected from the group consisting of Methotrexate, Pemetrexed, Pralatrexate and Raltitrexed whereby Methotrexate and Pemetrexed are particularly preferred.

Such compounds are anticancer drugs and therefore are of high commercial interest.

In a further embodiment of the reaction, chloroacetonitrile which is an inexpensive and commercially available material is used in the esterification reaction for producing the compounds of formula (II) or their precursors.

The esterification reaction is carried in a polar solvent, more preferably in a water miscible polar solvent, especially a solvent selected from the group consisting of dimethylformamide, dimethylacetamide, dimethylsulfoxide, a ketono like acetone or methylisobutyl ketone and acetonitrile or mixtures thereof.

It has been shown that for this kind of reaction, particularly DMF, give the best results with regard to yield as well as solubility of the starting materials or their salts. After formation of cyanometester of formula (II) or their intermediates, water can be added to reaction mixture and the corresponding ester is precipitated and isolated by filtration.

Precipitation is a particularly preferred method for isolating the formed cyanomethylesters of formula (II) or their intermediates since it can be affected by simply stirring the mixture at room temperature without the need for more complex purification technique such as column chromatography.

In a further embodiment of the invention, glutamic acid precursors of compounds of formula (II) are reacted with the chloroacetonitrile at a temperature from 20 to 120° C., preferably from 50 to 80° C.

In another embodiment of the invention, the cyanomethyl ester of glutamic acid or its N-substituted derivatives are coupled with other intermediates containing heterocyclic rigs having haloalkyl or carboxyl groups to give compounds of formula (II).

The coupling reaction are carried out in water or in an organic solvent, especially polar solvents give the best results with regard to yield as well as solubility of all agents involved. Dimethylformamide, dimethylacetamide, and water, have thereby been shown to be the most suitable solvents at a temperature from 0 to 100° C., preferably from 50 to 75° C.

When water is used as a solvent compounds of formula (II) directly precipitated from the reaction mixtures in a pH range about 1 to about 6, preferably in a pH range about 2 to about 5, especially pH about 4.0 at a temperature from 0 to 60° C., preferably from 0 to 25° C.

It has been found that in the above-named temperature ranges, the reactions can be performed in 0.5 to 4.5 hours, preferably 1 hour for obtaining a good yield.

In a further embodiment of the invention, the compound of formula (II) are reacted with the metal hydroxide, earth alkali hydroxides or carbonates to give the compounds of formula (I) or their salts.

The hydrolysis reaction is carried out in a water/alcohol mixture in the presence of 1 to 3 equivalents, especially 2 equivalents of metal hydroxide, alkaline earth metal hydroxides or carbonates. Polar solvents give the best results with regard to yield as well as solubility of all agents involved. Hydrolysis of cyanomethyl groups is done at a temperature from 0 to 100° C., preferably from 20 to 25° C.

It has been found that in the above-named time ranges a virtually complete hydrolysis reaction is achieved leading to high yields with high analytical and optical purity of the compound of formula (I) or their pharmaceutically useful salts.

The salt form of the compounds of formula (I) are obtained by suspending the compounds of formula (I) into water, adjusting the pH to about 10 with corresponding metal hydroxide and then adding them to a ketone such as acetone to precipitate.

It is understood that the above features and the features described below can be used not only in their described combination but also in other combinations or in isolation without departing from the scope of the invention.

The invention is now further illustrated by means of examples. These examples are not intended to limit the scope of the invention any way.

EXAMPLE 1

Preparation of N-[4-(methylamino)benzoyl]-L-glutamic Acid Disodium Salt from N-[4-(methylamino)benzoyl]-L-glutamic Acid Zinc Salt A 1 l erlenmayer equipped with magnetic stirrer was charged with 500 ml of water and 50 gr (0.15 mol) of N-[4-(methylamino)benzoyl]-L-glutamic acid zinc salt (~0.85% pure) at room temperature. The pH of the mixture was adjusted to 8.0 by using 0.2M $Na_2CO_3$. The precipitate Zinc oxide was isolated via filtration. The pH of the solution was adjusted to 6.2 by using dilute HCl. The solvent evaporated under reduced pressure and the residue was dried under vacuum at 50° C. for 5-6 hours to give 36.1 g (0.116 mol) of N-[4-(methylamino)benzoyl]-L-glutamic acid disodium salt in 90% yield as a red foam.

EXAMPLE 2

Preparation of Dicyanomethyl N-[4-(methylamino) benzoyl]-L-glutamic Acid from N-[4-(methylamino) benzoyl]-L-glutamic Acid Disodium Salt A 1 L flask was equipped with magnetic stirrer, thermometer and condenser. The flask was charged with 250 ml of DMF, 30 g (0.096 mol) of N-[4-(methylamino)benzoyl]-L-glutamic acid disodium salt and 20 ml (0.31 mol) of chloroacetonitrile at room temperature. The suspension was stirred at 60° C. for 4-5 hours. The solution was cooled to room temperature and 250 ml of water was added. The mixture was stirred for 15-20 minutes, a white precipitate was formed. The solid was isolated via filtration and washed with 20 ml of water. The solid was dried under vacuum at 50° C. for 3 hours and Dicyanomethyl N-[4-(methylamino)benzoyl]-L- glutamic acid_was obtained 27 g (0.078 mol) as a white solid in 81% yield. According to $^1$H-NMR the product was very clean.

$^1$H-NMR (DMSO) δ 2 07 (m, 2H), 2.55 (t, 2H), 2.70 (d, 3H), 4.45 (m, 1H), 4.91 (s, 2H), 4.97 (s, 2H), 6.23 (q, 1H), 6.53 (d, 2H), 7.65 (d, 2H), 8.43 (d, 1H).

EXAMPLE 3

Preparation of dicyanomethyl N-[4[[(2,4-diamino-6-pteridinyl)methyl]methylamino]benzoyl]-L-glutamate (Methotrexate Dicyanomethyl Ester)

A 1 L flask was equipped with magnetic stirrer, thermometer and condenser. The flask was charged with 143 ml of water and 10 g (0.029 mol) of 2,4-Diamino-6-(bromomethyl) pteredine hydrobromide at room temperature. To this suspension was added 13 g (0.037 mol) of Dicyanomethyl N-[4-(methylamino)benzoyl]-L-glutamic acid at room temperature. The pH of the mixture was 2.40. The mixture was heated to 58-62 C and stirred there for 1 hour. The progress of the reaction was followed by TLC (EtOAc:MeOH, 4:1) and it was completed. The mixture was cooled to room temperature and the solid was isolated by filtration. The solid cake was washed with 15 ml of water and dried under vacuum at 50° C. for 5-6 hours to give 13.2 g (0.029 mol) of Methotrexate Dicyanomethyl ester as a yellow solid in 87% yield. According to $^1$H-NMR the product was very clean.

$^1$H-NMR (DMSO) δ 2 08 (m, 2H), 2.55 (t, 2H), 3.23 (s, 3H), 4.46 (m, 1H), 4.82 (d, 2H), 4.94 (s, 2H), 4.98 (s, 2H), 6.82 (d, 2H), 7.35 (m, 2H), 7.72 (d, 2H), 8.30 (s, 1H), 8.52 (d, 2H), 8.64 (s, 1H).

EXAMPLE 3

Preparation of N-[4[[(2,4-diamino-6-pteridinyl)methyl]methylamino]benzoyl]-L-glutamic Acid Disodium Salt from Methotrexate Dicyanomethyl Ester A 1 L flask was equipped with magnetic stirrer, thermometer and condenser. The flask was charged with 160 ml of methanol, 80 ml of water and 1.75 g (0.03 mol) of KOH. The solution was stirred at rt for 5-10 minutes. To this solution was added 10 g (0.019 mol) of Methotrexate Dicyanomethyl ester at room temperature. The solution was stirred for 20 min at room temperature. The progress of the reaction was followed by TLC (EtOAc:MeOH 4:1) and it was completed. The solution was concentrated under reduced pressure. The pH of the solution was adjusted to 4.2 with dilute HCl and a yellow solid was precipitated. The crude methotrexate was isolated by filtration and washed with water. The wet cake was suspended into 75 ml water and the pH was adjusted to 10 with 2N NaOH, a clear solution was obtained. To the solution 2 g of charcoal was added stirred for 5 min. and filtered. The solution containing methotrexate disodium was added at room temperature into 500 ml of acetone while stirring. A yellowish solid was formed and isolated by filtration. The solid was dried under vacuum at 50° C. for 8-10 hours to yield 8.3 g (0.017 mol, 89% yield) of Methotrexate Disodium with a purity of higher than 99.8% determined by HPLC.

$^1$H-NMR (D$_2$O) δ 1.88 (m, 1H), 1.98 (m, 1H), 2.17 (m, 2H), 2.89 (s, 3H), 4.14 (m, 1H), 4.37 (s, 2H), 6.53 (d, 2H), 7.46 (d, 2H), 8.27 (s, 1H).

The invention claimed is:

1. A method for producing antifolate agents having a glutamic acid part in their structure or salt thereof with the general formula

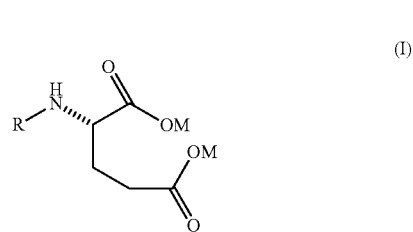

(I)

wherein
M is a monovalent or divalent cation selected from group consisting of Na$^+$, K$^+$, ½Ca$^{++}$ or ½Mg$^{++}$; and
R is

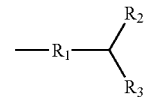

with
R$_1$ being a carbonyl group; and
R$_2$ and R$_3$ being the same or different and being selected from the group consisting of
(i) straight-chain or branched, saturated or unsaturated C$_1$-C$_{20}$-heteroalkyl groups, which can optionally be substituted with amino groups; and
(ii) aromatic or aliphatic C$_3$-C$_{18}$-hydrocarbon rings, which can optionally be substituted with one or more selected from the group consisting of alkyl, alkenyl, alkynyl, carboxyl, hydroxyl, amine, nitro, thiol, sulfoxyl, sulfone groups, which can optionally be substituted and/or form further rings; and
(iii) aromatic or aliphatic C$_3$-C$_{18}$-heterocycles, which can optionally be substituted with one or more selected from the group consisting of alkyl, alkenyl, alkynyl, carboxyl, hydroxyl, amine, nitro, thiol, sulfoxyl, sulfone groups, which can optionally be substituted and/or form further rings;
whereby R$_2$ and R$_3$ together can form an aromatic or aliphatic C$_3$-C$_{18}$-heterocycle, which can optionally be substituted with one or more selected from the group consisting of alkyl, alkenyl, alkynyl, carboxyl, hydroxyl, amine, nitro, thiol, sulfoxyl, sulfone groups, which can optionally be substituted and/or form further rings;
comprising reacting a compound of the following formula

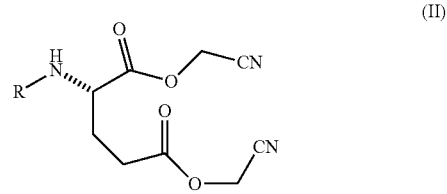

(II)

wherein R is the same as in formula (I), with an acid or base in a solvent; and the compounds of formula (II) are obtained from reacting glutamic acid, N-substituted glutamic acids or their salts with chloroacetonitrile.

2. The method according to claim 1, wherein R$_2$ and R$_3$ together form a phenyl ring, which can be substituted with an alkyl group or alkyl group containing hetero atoms and alkyl groups can be further substituted with a bicyclic or heterocyclic ring systems containing structures like purines or pyrimidenes.

3. The method according to claim 1, wherein the compound of formula (I) is a compound that shows antifolate activity and used to treat different types of cancers.

4. The method according to claim 3, wherein the compound of formula (I) is selected from the group of consisting of Methotrexate, Pemetrexed, Pralatrexate and Raltitrexed.

5. The method according to claim 4, wherein the compound of the formula (I) is selected from the group consisting of Methotrexate and Pemetrexed.

6. The method according to claim 1, wherein cyanomethyl ester of the compounds of formula (II) or their intermediates having glutamic acid part are easily prepared starting from metal salt of glutamic acid or from its N-substituted derivatives by reacting with chloroacetonitrile.

7. The method according to claim 6, wherein the esterification reaction is carried in a polar solvent, more preferably in a water miscible polar solvent.

8. The method according to claim 7, wherein the solvent is selected from the group consisting of dimethylformamide, dimethylacetamide, dimethylsulfoxide, acetone, methylisobutyl ketone and acetonitrile or mixtures thereof.

9. The method according to claim 1, wherein the cyanomethyl ester of glutamic acid or its N-substituted derivatives are coupled with other intermediates containing heterocyclic rings having haloalkyl or carboxyl groups to give compounds of formula (II).

10. The method according to claim 9, wherein the coupling reaction affording compounds of formula (II) are carried out in water or in an organic solvent, such as dimethylformamide and dimethylacetamide.

11. The method according to claim 10, wherein the coupling reaction is carried out at a temperature from 0 to 100.degree. C., preferably from 50 to 75.degree. C.

12. The method according to claim 1, wherein the compounds of formula (II) are reacted with the metal hydroxide, alkaline earth metal hydroxides or carbonates to give the compounds of formula (I) or their salts.

13. The method according to the claim 12, wherein the reaction is carried out in a water/alcohol mixture in the presence of 1 to 3 equivalents, especially 2 equivalents of metal hydroxide, earth alkali hydroxides or carbonates.

14. The method according to claim 13, wherein the reaction of both cyanomethyl groups is done at a temperature from 0 to 100° C., preferably from 20 to 25.degree. C.

15. The method according to claim 1, wherein the salt form of the compounds of formula (I) are obtained by suspending the compounds of formula (I) into water, adjusting the pH to about 10 with corresponding metal hydroxide and then adding them to a ketone such as acetone to precipitate.

* * * * *